(12) United States Patent
Kozloski et al.

(10) Patent No.: US 10,345,988 B2
(45) Date of Patent: Jul. 9, 2019

(54) CURSOR AND CURSOR-HOVER BASED ON USER STATE OR SENTIMENT ANALYSIS

(71) Applicant: International Business Machines Corporation, Armonk, NY (US)

(72) Inventors: James R. Kozloski, Fairfield, CT (US); Clifford A. Pickover, Yorktown Heights, NY (US); Maja Vukovic, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 745 days.

(21) Appl. No.: 15/071,552

(22) Filed: Mar. 16, 2016

(65) Prior Publication Data
US 2017/0269814 A1    Sep. 21, 2017

(51) Int. Cl.
G06F 3/0484 (2013.01)
G06F 3/0481 (2013.01)
G06F 3/01 (2006.01)
G06F 3/0486 (2013.01)
A61B 5/11 (2006.01)
(Continued)

(52) U.S. Cl.
CPC ............ *G06F 3/04812* (2013.01); *A61B 5/11* (2013.01); *A61B 5/165* (2013.01); *A61B 5/168* (2013.01); *A61B 5/4088* (2013.01); *G06F 3/012* (2013.01); *G06F 3/015* (2013.01); *G06F 3/0486* (2013.01); *G06F 3/04842* (2013.01); *A61B 5/0077* (2013.01); *A61B 5/1128* (2013.01); *A61B 5/4266* (2013.01)

(58) Field of Classification Search
CPC .................................................. G06F 3/04842
See application file for complete search history.

(56) References Cited

U.S. PATENT DOCUMENTS

| | | | | | |
|---|---|---|---|---|---|
| 5,819,055 A | * | 10/1998 | MacLean | ............ | G06F 3/0481 715/798 |
| 5,995,101 A | * | 11/1999 | Clark | ............... | G06F 3/04895 715/711 |

(Continued)

FOREIGN PATENT DOCUMENTS

CN        100399336 C        7/2008

OTHER PUBLICATIONS

Anonymously; "Hover-Over Content for User Interfaces"; http://ip.com/IPCOM/000236793; May 15, 2014.

(Continued)

*Primary Examiner* — Ryan Barrett
(74) *Attorney, Agent, or Firm* — Cahn & Samuels, LLP

(57) ABSTRACT

An embodiment of the invention provides a method for displaying a text box on a display screen of an electronic device, including determining a state of a user with an input device having a camera, a keyboard, and/or a mouse. A text box setting on the electronic device is modified with a processor connected to the input device based on the state of the user, the modifying of the text box setting includes modifying an amount of visual information in the text box, modifying an amount of audible information played with the text box, and/or modifying an amount of time required to display the text box. The text box is displayed on the display screen of the electronic device when a pointer is within a threshold degree of proximity to an item on the display screen for the amount of time required to display the text box.

20 Claims, 6 Drawing Sheets

(51) Int. Cl.
*A61B 5/16* (2006.01)
*A61B 5/00* (2006.01)

(56) References Cited

U.S. PATENT DOCUMENTS

| | | | | |
|---|---|---|---|---|
| 6,008,809 | A * | 12/1999 | Brooks | G06F 3/0481 715/792 |
| 6,606,101 | B1 * | 8/2003 | Malamud | G06F 3/04812 715/715 |
| 7,480,863 | B2 | 1/2009 | Branson et al. | |
| 8,140,971 | B2 | 3/2012 | Branson et al. | |
| 2002/0105427 | A1 * | 8/2002 | Hamamoto | G06Q 10/02 340/576 |
| 2004/0027383 | A1 * | 2/2004 | Jaeger | G06F 3/0481 715/769 |
| 2004/0098462 | A1 * | 5/2004 | Horvitz | G05B 19/404 709/207 |
| 2005/0091096 | A1 * | 4/2005 | Coates | G06Q 10/047 705/7.26 |
| 2005/0114778 | A1 * | 5/2005 | Branson | G06F 9/453 715/711 |
| 2005/0270307 | A1 * | 12/2005 | Jacques Brouaux | G06F 3/0481 345/619 |
| 2006/0104276 | A1 | 5/2006 | Naick et al. | |
| 2006/0236328 | A1 * | 10/2006 | DeWitt | G06F 9/452 719/329 |
| 2007/0192719 | A1 | 8/2007 | Chellis et al. | |
| 2009/0307627 | A1 * | 12/2009 | Adams | G06F 9/451 715/781 |
| 2010/0075652 | A1 * | 3/2010 | Keskar | H04M 1/72569 455/418 |
| 2011/0078625 | A1 * | 3/2011 | Mumford | G06F 9/451 715/804 |
| 2012/0288845 | A1 | 11/2012 | Kumar | |
| 2012/0323933 | A1 * | 12/2012 | He | G06Q 10/107 707/749 |
| 2013/0275899 | A1 * | 10/2013 | Schubert | G06F 3/0481 715/765 |
| 2013/0298034 | A1 * | 11/2013 | Ramachandran | G06F 9/451 715/748 |
| 2014/0157201 | A1 | 6/2014 | Ronkainen | |
| 2014/0267130 | A1 | 9/2014 | Hwanf et al. | |
| 2015/0106741 | A1 * | 4/2015 | Friend | H04L 51/16 715/752 |
| 2015/0188871 | A1 * | 7/2015 | Lewis | H04L 51/24 709/207 |
| 2015/0261387 | A1 * | 9/2015 | Petersen | G06F 3/013 715/765 |
| 2016/0037481 | A1 * | 2/2016 | Won | H04W 68/00 715/771 |
| 2016/0315842 | A1 * | 10/2016 | Boss | H04L 65/80 |
| 2017/0168703 | A1 * | 6/2017 | Feris | G06F 3/04855 |
| 2017/0334456 | A1 * | 11/2017 | Deligianni | A61B 5/18 |
| 2017/0344209 | A1 * | 11/2017 | Gordon | G06F 3/013 |
| 2018/0125405 | A1 * | 5/2018 | Yamada | A61B 5/165 |
| 2018/0125406 | A1 * | 5/2018 | Yamada | A61B 5/165 |
| 2018/0218268 | A1 * | 8/2018 | Kozloski | G06N 3/008 |
| 2018/0248930 | A1 * | 8/2018 | Boss | H04L 65/80 |
| 2018/0293528 | A1 * | 10/2018 | Bostick | G06Q 10/06316 |
| 2018/0325441 | A1 * | 11/2018 | Deluca | A61B 5/165 |

OTHER PUBLICATIONS

IBM; "Method to Improve Readability and Edibility on Graphical User Interface (GUI) Elements"; http://ip.com/IPCOM/000176696; Nov. 20, 2008.
Wikipedia; "Balloon Help" [retrieved on Jan. 7, 2016]. Retrieved from the Internet: <URL: https://en.wikipedia.org/wiki/Balloon_help>.
Wikipedia; "Hoverbox" [retrieved on Jan. 7, 2016]. Retrieved from the Internet: <URL: https://en.wikipedia.org/wiki/Hoverbox>.
Wikipedia; "Mouseover" [retrieved on Jan. 7, 2016]. Retrieved from the Internet: <URL: https://en.wikipedia.org/wiki/Mouseover>.
Wikipedia; "Status bar" [retrieved on Jan. 7, 2016]. Retrieved from the Internet: <URL: https://en.wikipedia.org/wiki/Status_bar>.
Wikipedia; "Tooltip" [retrieved on Jan. 7, 2016]. Retrieved from the Internet: <URL: https://en.wikipedia.org/wiki/Tooltip>.

* cited by examiner

US 10,345,988 B2

CURSOR AND CURSOR-HOVER BASED ON USER STATE OR SENTIMENT ANALYSIS

BACKGROUND

The present invention relates to systems, methods, and computer program products for cursor and cursor-hover based on user state or sentiment analysis.

A tooltip, infotip, or hint is a common graphical user interface element used in conjunction with a cursor. The user hovers the pointer over an item, without clicking it, and a tooltip may appear, e.g., a small "hover box" with information about the item being hovered over. Balloon help displays help text in "balloons", like those containing the words in a comic strip. The name is used to refer to any sort of pop-up help text.

A mouseover, mouse hover, or hover box is a graphical control element that is activated when the user moves or "hovers" the pointer over its trigger area, usually with a mouse, but also possible using a digital pen. The graphical control element is particularly common in web browsers where the URL of a hyperlink can be viewed in the status bar. Site designers can define their own mouseover events using JavaScript and/or Cascading Style Sheets. In case of multiple layers, the mouseover event is triggered by the uppermost layer. Mouseover events are not limited to web design and are commonly used in modern GUI programming. Their existence might not even be known to the user as the events can be used to call any function and might affect only the internal workings of the program.

A hoverbox is a popup window that appears when the mouse is placed over an icon on the screen for a short period of time without clicking. Hoverboxes can differ from tooltips in that hoverboxes support HTML elements and can be used to display forms, graphics and lists among other html elements. Hoverboxes can differ from traditional popups in that the user must hover over a page element to activate. Hoverboxes are typically used to hide page elements that would otherwise clutter a website.

A status bar is a graphical control element which poses an information area typically found at the window's bottom. It can be divided into sections to group information. Its job is primarily to display information about the current state of its window, although some status bars have extra functionality. For example, many web browsers have clickable sections that pop up a display of security or privacy information.

SUMMARY OF THE INVENTION

An embodiment of the invention provides a method for displaying a text box on a display screen of an electronic device. The state of a user is determined with an input device (e.g., camera, keyboard, mouse) from a facial expression of the user, a degree of multitasking of the user, information from a calendar of the user, and/or brain waves of the user. A processor connected to the input device modifies a text box setting on the electronic device based on the state of the user. The modification(s) can include modifying the amount of visual information in the text box, modifying the amount of audible information played with the text box, and/or modifying the amount of time required to display the text box. The text box is displayed on the display screen of the electronic device when a pointer is within a threshold degree of proximity to an item on the display screen for the amount of time required to display the text box.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

Figure 1:
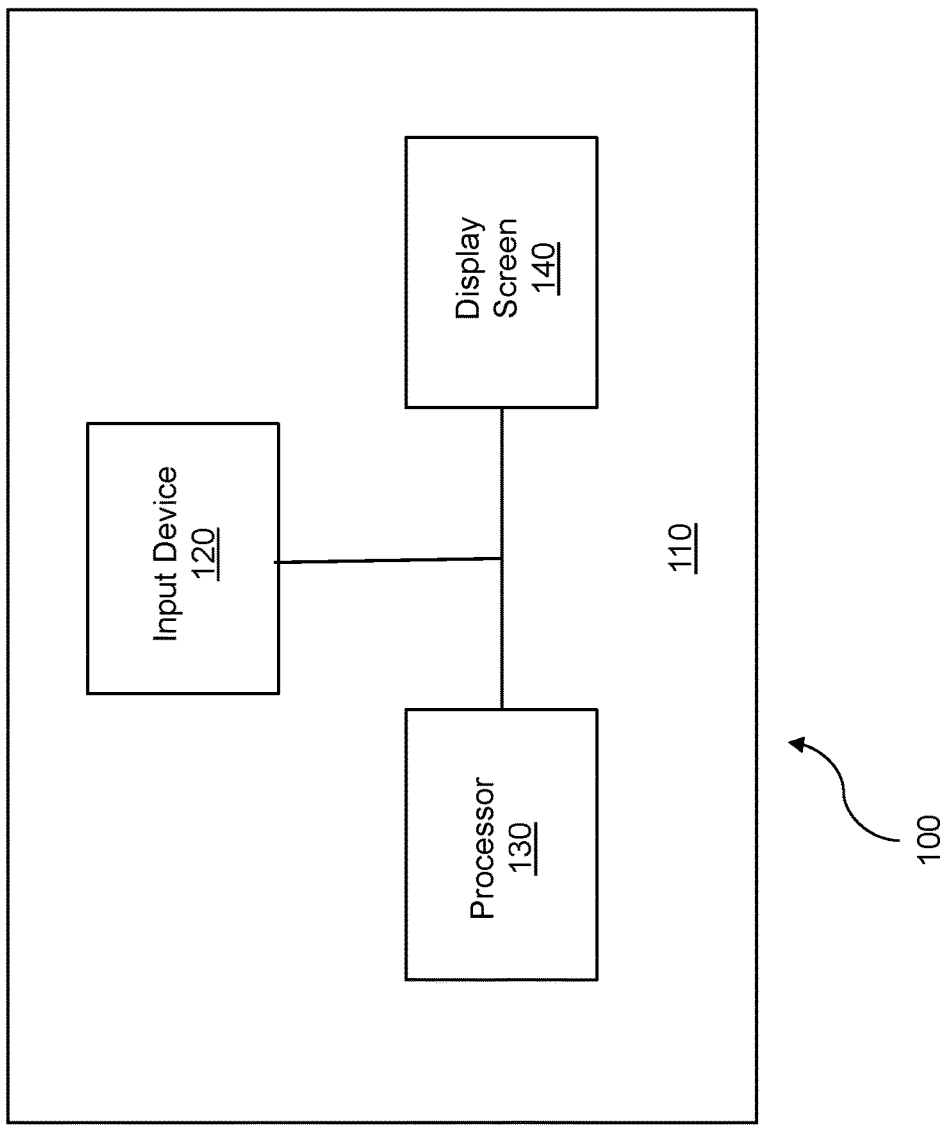
FIG. 1 is a diagram illustrating a system for displaying a text box on a display screen of an electronic device according to an embodiment of the invention.
Figure 2:
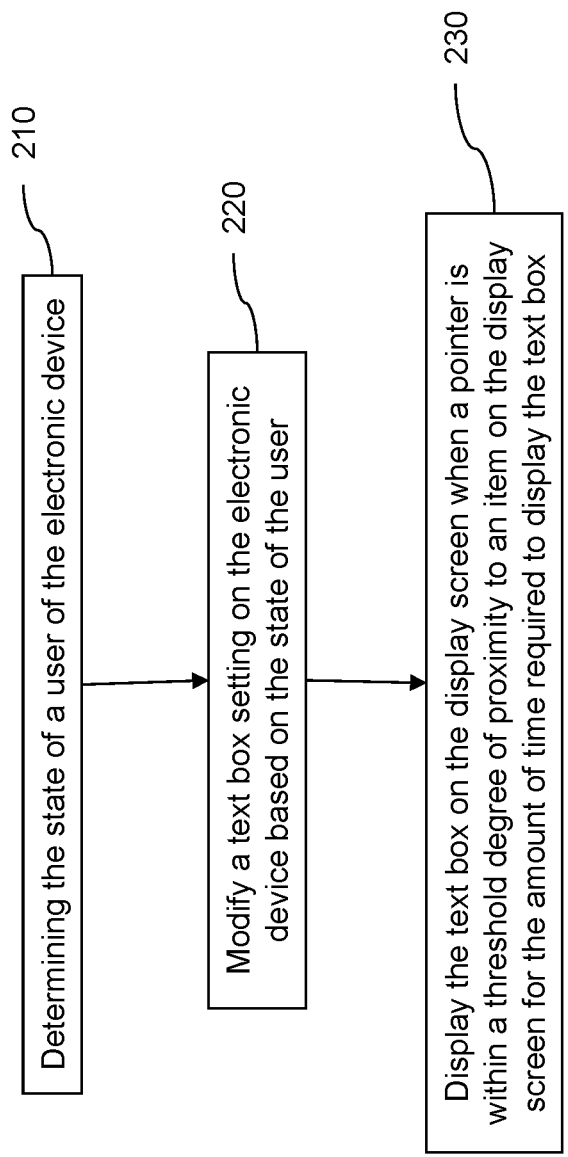
FIG. 2 is a flow diagram illustrating a method for displaying a text box on a display screen of an electronic device according to an embodiment of the invention.

FIG. 1 illustrates a system 100 for displaying a text box (e.g., a hover box, tooltip, infotip) on a display screen of an electronic device according to an embodiment of the invention. FIG. 2 is a flow diagram illustrating a method for displaying a text box on a display screen of an electronic device according to an embodiment of the invention (e.g., using the system 100).

The state of a user of the electronic device 110 can be determined with an input device 120 (210). The input device 120 (also referred to herein as a "means for determining a state of a user") can be a camera, a keyboard, a mouse, and/or a brain wave monitor (e.g., electroencephalography (EEG) monitor). Although FIG. 1 illustrates an embodiment where the input device 120 (e.g., camera) is physically on the electronic device 110 (e.g., mobile telephone), it is recognized that in another embodiment, the input device 120 (e.g., brain wave monitor) is connected to the electronic device 110 (e.g., desktop computer) wirelessly. As used herein, the term "connected" includes operationally connected, logically connected, in communication with, physically or wirelessly connected, engaged, coupled, contacts, linked, affixed, and attached.

The state of the user can be determined from a facial expression of the user, a degree of multitasking of the user, information from a calendar of the user, and/or physiological signals (e.g., brain waves) of the user. For example, a processor determines that the user is fatigued, frustrated, and/or young from a photograph of the user's face. In another example, the processor determines that the user is fatigued because the user's calendar indicates that he has had multiple long meetings during the day, or the user is currently in a meeting. In yet another example, the processor monitors the performance of the user, through the interaction with a computer system, and/or the user's speech pattern (e.g., through voice recognition and tone assessment) to determine that the user is fatigued. In addition, the system 100 can include user interfaces (e.g., electrodes, heart monitor) to monitor skin conductivity, the user's heart rate, sweating of palms, etc. to determine that the user is frustrated. The system can also administer a cognitive test (e.g., a computer generated game) to track the user's reaction time.

In at least one embodiment, the system 100 tracks the user's eyes (e.g., with a camera) and the processor can determine that the user is distracted when the user's eyes are directed away from the camera for a predetermined amount of time, a predetermined number of times, in a predetermined period of time (e.g., for more than 5 seconds, 10 times, in 10 minutes). The eye tracking process can only be active when the user is using the system 100. The processor can also determine that the user is distracted if the user is engaged in a telephone call or video conference.

In addition, the processor can determine that the user is a youth from the user's profile. The user's profile can be created when the user registers for the electronic device 110 and/or the system 100. The processor can obtain the user's profile online (e.g., social media account, public records). The processor can also determine that the user is a youth from the user's preferences, browsing history, and/or type of social network.

In at least one embodiment, the processor can determine that the user is autistic, has Alzheimer's or pre-Alzheimer's, a learning disability, and/or attention deficit hyperactivity disorder from the user's profile. The profile can be automatically created by the system 100 or affirmatively created by the user, an assistant of the user, and/or a guardian of the user. The processor can also determine that the user is autistic by observing atypical eye contact, lack of social activity, and/or slow responses—either to other people or systems. An autistic profile can be built over the time. The processor can also determine that the user has Alzheimer's by detecting that the user is confused, experiences loss of memory, and/or difficulty in understanding concepts presented. The user can also be presented with a test on visual/spatial relationships by the system 100. The processor can also determine that the user has pre-Alzheimer's by detecting mood changes by the user, that the user is confused, experiences loss of memory, and/or difficulty in understanding concepts presented. The user can also be presented with a test on visual/spatial relationships by the system 100 to determine whether the user has Alzheimer's or pre-Alzheimer's. Additionally, the processor can determine that the user has a learning disability and/or attention deficit hyperactivity disorder by monitoring user interaction with the system 100.

In at least one embodiment of the invention, a processor 130 connected to the input device 120 modifies a text box setting on the electronic device 110 based on the state of the user (220). The text box setting can include the amount of visual information in the text box, the amount of audible information played with the text box, and/or the amount of time required to display the text box (also referred to herein as the amount of time of hover). As used herein, the term "processor" includes a computer hardware device (e.g., CPU, microprocessor) that modifies a text box setting on the electronic device.

For example, the processor 130 (also referred to herein as a "means for determining a state of a user", a "means for modifying a text box setting on the electronic device", a "means for determining the degree of multitasking of the user", and/or a "means for creating a composite text box") can decrease the amount of visual information in the text box when the state of the user includes fatigue, frustration, distracted, autistic, youth, Alzheimer's, pre-Alzheimer's, learning disability, and/or attention deficit hyperactivity disorder. The processor 130 can increase the amount of audible information in the text box when the state of the user includes fatigue, frustration, distracted, autistic, youth, Alzheimer's, pre-Alzheimer's, learning disability, and/or attention deficit hyperactivity disorder. Moreover, the processor 130 can decrease the amount of time required to display the text box when the state of the user includes fatigue, frustration, distracted, autistic, youth, Alzheimer's, pre-Alzheimer's, learning disability, and/or attention deficit hyperactivity disorder.

In at least one embodiment of the invention, the processor is on a single integrated circuit (IC), or on a few integrated circuits, and includes an arithmetic logic unit (ALU), which performs arithmetic and logical operations and a control unit (CU), which extracts instructions from memory and decodes and executes the instructions, calling on the ALU when necessary. The ALU can perform operations such as addition, subtraction, and operations such as AND or OR. Each operation of the ALU can set one or more flags in a status register, which may indicate the results of the last operation (zero value, negative number, overflow, or others). The control logic can retrieve instruction codes from memory and initiate the sequence of operations required for the ALU to carry out the instruction. The processor can contain multiple metallic connectors or pins on the underside, where the processor can be inserted directly into a socket, pin side down, on the motherboard. The processor can also have an attached heat sink and small fan that go directly on top of the processor to help dissipate heat.

The text box can be displayed on the display screen 140 of the electronic device 110 when a pointer (e.g., cursor) is within a threshold degree of proximity to an item (e.g., icon, toolbar, hyperlink, text input field) on the display screen 140 for the amount of time required to display the text box (also referred to herein as the amount of time of hover) (230). For example, when a cursor is within 2 mm of a text input field on a webpage or mobile application for 2 or more seconds, a text box is displayed next to the text input field that provides visual information (text, images, or video) regarding the text input field. For instance, the text box can include recommendations or instructions on what to enter into the text input field. In another example, when a cursor is on a link or icon representing a movie, a text box is displayed with information about the movie. In at least one embodiment, the display screen is a touch screen that includes a finger detection system, where the pointer appears on the display screen when a finger or stylus is within a threshold distance (e.g., 1 mm) to the display screen.

In at least one embodiment of the invention, the degree of multitasking of the user is determined from the rate of switching between applications on the electronic device 110, the rate of switching between windows on the electronic device 110, the number of open applications on the electronic device 110, the number of open windows on the electronic device 110, and/or information from the calendar of the user. For example, a numerical rating system is used where a higher score indicates that the user is distracted and a lower score indicates that the user is not distracted. In at least one embodiment, a score of 0 is assigned if the user switches applications or windows 1-2 times/minute; a score of 1 is assigned if the user switches applications or windows 3-6 times/minute; and, a score of 2 is assigned if the user switches applications or windows 7 or more times/minute. The number of open applications on the electronic device 110 can exclude system monitoring or background applications. The number of open applications on the electronic device 110 can only include applications that are visible on the display screen, the task bar, or in the task manager.

In another embodiment, a score of 0 is assigned if 0-3 applications and/or windows are running on the electronic device 110; a score of 1 is assigned if 4-7 applications and/or windows are running on the electronic device 110; and, a score of 2 is assigned if 8 or more applications and/or windows are running on the electronic device 110. In yet another embodiment, a score of 0 is assigned if the user's calendar indicates 0-1 tasks and/or events in the past 3 hours; a score of 1 is assigned if the user's calendar indicates 2-3 tasks and/or events in the past 3 hours; and, a score of 2 is assigned if the user's calendar indicates 4 and/or more tasks or events in the past 3 hours. The scores can be combined to calculate a total score for the user. When it is determined that the user is distracted, the text box setting can be modified to decrease the amount of visual information in the text box, increase the amount of audible information in the text box, and/or decrease the amount of time required to display the text box. The processor 130 can block the audible information if the calendar indicates that the user is in a meeting or telephone call.

In at least one embodiment of the invention, the processor 130 creates a composite text box when the user drags a first text box to a position proximate a second text box. The composite text box can include information from the first text box, information from the second text box, and/or information describing how the first text box relates to the second text box. For example, the user clicks on a first text box (including information regarding an icon) drags the first text box onto a second text box (including information regarding a hyperlink), and releases the first text box onto the second text box.

The processor 130 can create a composite text box that includes some of the information from the first text box, some of the information from the second text box, and information describing how the icon relates to the hyperlink. In at least one embodiment, the composite text box is displayed on the display screen 140 (also referred to herein as a "means for displaying the text box on the display screen of the electronic device") when display of the first text box is triggered (e.g., cursor is positioned on the icon) and/or when display of the second text box is triggered (e.g., cursor is positioned within 5 mm of the hyperlink).

In addition, the processor 130 can identify that a text box satisfies a threshold degree of importance based on the state of the user and display the text box on the display screen 140 when the pointer is not within the threshold degree of proximity to the item on the display screen for the amount of time required to display the text box. For example, the processor 130 determines that a text box relating to a hyperlink for network provisioning has a degree of importance of 7 based on the state of the user (e.g., user is alert and interested in VLANs).

Because the degree of importance of the textbox is greater than the threshold degree of importance (e.g., 6), the text box is displayed even though the pointer is not within the threshold degree of proximity to the item on the display screen 140 (e.g., 1 mm) for the amount of time required to display the text box (1 second). In other words, because the text box is important based on the state of the user, the text box is displayed even though the pointer is not near the trigger item on the display screen 140.

In at least one embodiment of the invention, the processor 130 modifies the text box setting on the electronic device 110 based on a profile of the user, where the profile of the user includes a browsing history of the user, purchasing history of the user, application history of the user, text box history of the user (e.g., a list of text boxes have been displayed to the user and when they were displayed), electronic bookmarks of the user, likes (e.g., items that the user has liked on social media), and interests of the user. For example, the system maintains a browsing history of the user and identifies that over the past 24 hours, the user has been increasingly checking content about transformation of web applications to the cloud. Based on the content assessed, the system can reason about familiarity level of the user with this topic. As the user accesses a blog about transformation to microservices architectures (a type of cloud application architecture), text boxes can explain what microservices are, as the user has not previously read about this concept.

In another example, a user has been purchasing baby toys, in particular for infants up to 12 months old. A text box may be adapted to explain the terms pertaining to the different motor and cognitive skills that infants up to 12 months may need to acquire and highlight them in text boxes. In yet another example, the application history of a user may drive the decisions about what is important to the user. If a user continuously uses XCode and program in swift, new terminology and features of swift may be described in text boxes. In still another example, the text box history helps the system reason about a user's interest in particular terms/concepts and level of competency in the same. The system can determine that by now the user is familiar and has continuously been viewing text boxes with information about sorting and stackable toys for babies and the system prevents these text boxes from displaying in future webpages so as not to overwhelm the user.

In at least one embodiment of the invention, the system learns the user's skills and knowledge and ensures that text boxes (in general or for specific classes) are not overlooked or dismissed easily by the user. For example, if the user has above a threshold number of bookmarks about image migration using a specific tool and is not following the correct configuration, as explained in tooltips, the system enlarges and/or enforces the tooltips to stay open/visible longer. In some cases, text boxes that would normally require a mouseover event to trigger them may become "forced" reveals (even if the user does not hover) when certain information is deemed important based on a user's cognitive state, history, history of use with an application or procedure, etc.

In at least one embodiment, the system learns about user's "likes" and preferences through social media to determine which text boxes will be displayed and which text boxes will not be displayed. If a user continuously likes a specific type of music, text boxes related to that style of music can be highlighted, enlarged, or otherwise adjusted to engage the user.

At least one embodiment of the invention provides a method and system that includes a graphical user interface (GUI) that supports mouseover, hoverbox, or tooltips GUI features. Based on a real-time assessment of a user's emotional state, the content or presentation of the GUI features can be changed from a default content, presentation, or timing. The change in GUI features may include a change in the amount of information, a change in the modality of information presentation (e.g., addition or subtraction of sounds, media, tactile feedback, transition to a 3-D virtual world, etc.), and/or a change in nature and length of text.

The emotional state may include the user's distraction level, fatigue, frustration, etc. The emotional state can be estimated by a user's facial expression, degree of multitasking (e.g., rate of switching between windows on a GUI), electronic calendar information (e.g., the user may have had many meetings during the day, the user is in a meeting, etc.), brain waves, etc. In at least one embodiment, the state of the user is determined from analysis of the user's speech, skin conductivity of the user (example), a heart rate of the user, presence of sweat of the user (example), tracking of the eyes of the user, telephone records of the user, a profile of the user, online personal data of the user (e.g., age, gender, occupation, location, interests, hobbies, likes, connections, friends), internet search history of the user, preference settings of the user, and/or internet browsing history.

The time required to "unmask" the hover content may be changed. For example, a webpage has a text box annotation for every word on the webpage. A mouse hover over the words unmasks the text box annotations, which can be very distracting. The system can modify the time of hover required to unmask the text box annotations based on the user's email, calendar, previous web browsing, electronic books, etc. It is therefore possible to obtain information via "quick hovers" on subjects that interest the user, and require "long hovers" for annotations more esoteric to the user. The system can identify what the user is interested in and not interested in based on the user's profile, which can include the user's browsing, bookmarking, purchasing, and/or book reading history.

In at least one embodiment, the system deploys an "attentional hover" mechanism, by which through various modalities, a user's focus of attention is mapped to the user interface, and a hover function implemented. These modalities may include eye tracking, gaze detection, facial expression analysis, eye blinks, mouth movements, mouse over/cursor movements, and/or wearables signals such as heart rate, etc. These signals may then combine to give a confidence a user has dwelled or "hovered" on a specific user interface element or word of text, and the resulting text box annotation can be deployed. As used herein, the term "text box" or "text box annotation" includes a tooltip, balloon help, mouseover, mouse hover, hoverbox, and popup window.

The system can automatically adapt text box annotations based on context of text and emotional state of the user. The hover text (and level of detail) may change based on the user's mood, distraction level, fatigue, etc. For example, when a user is alert, more information is provided in the text box annotation in proportion to the assessed degree of alertness. A text box annotation can be provided for the phrase "network provisioning" for which the system can provide an explanation of a virtual local area network (VLAN) and why information is needed at a certain step of the software execution.

The text box annotation can include text, video, and/or audio, such as a computer animated video with audible help or instructions, which can be a function of a real-time assessment of a user's emotional state. The system can learn about what a user reads as it relates to hover needs. More specifically, the system can adapt the characteristics of the text box based on the user's emotional state, knowledge, and/or interests. One user's text box need not be the same as another user's text box.

In at least one embodiment, the system learns the user's skills and knowledge and ensures that text boxes (in general, or for specific classes, or in specific) are not overlooked or dismissed easily by the user. For example, when a user is performing image migration using a specific migration technology for the tenth time and not following the correct configuration as explained in tooltips, the system enlarges the text box, displays the text box for a longer period of time, and/or decreases the amount of time of hover required to display the text box.

In at least one embodiment, text boxes require a mouseover event (e.g., the cursor is on or proximate to an icon for a threshold amount of time) in order for the text box to be displayed. In another embodiment, the system performs "forced reveals" (i.e., displayed text boxes even when a mouseover event does not occur) when certain information is deemed important based on the user's emotional state, history, history of use with an application or procedure, etc.

The text box can include a virtual reality-like immersion that triggers additional sensory modalities (e.g., hearing, etc.) when the system deems a user would benefit (e.g., is not in meeting, etc.). The system can redirect the text box content to another electronic device, such as the user's mobile telephone, smart watch, smart glasses, etc. The system can use haptic output to alert the user of a text box, such as, for example, vibration of the mouse and/or mouse pad. This could have particular use in instances where text boxes are forced reveals when certain information is deemed important based on the user's emotional state, history, history of use with an application or procedure, etc.

By monitoring the engagement level of users with text boxes, gathered insights can be used to improve the user interface layout and formatting as well as the flow of operations in the software package/service. For example, if users repeatedly go back to the text box that explains what protection group is for replication service, this information may be better introduced ahead of time in the process of replication, or the self-service may be redesigned.

Furthermore, the user can drag one text box over another text box or another piece of text to achieve a "composite" effect to understand how terms relate to one another and enhancing user's learning experience. Also, in the act of dragging (or drag and drop) of text boxes, two or more separate text boxes may be combined to create a composite text box. In the future, triggering one of the text boxes can also trigger the display of the composite textbox, which can include information related to the previously separate text boxes. The system may also have applications for displaying header and cell information regarding entries in a table. The system can display a text box after a user moves a cursor over a user interface element shown on the display screen, and then a second text box can be displayed after invoking an element in the first text box while the pointer continues to be positioned over the user interface element.

In at least one embodiment, the electronic device can detect a user's finger at a location hovering over but not touching the display screen. A text box can be displayed when the user's finger is over a user interface element but not touching the display screen. The touch screen can detect that the user's fingers are proximate to the touch screen through capacitive sensing. Additionally, finger movement can be detected while the fingers are hovering.

Depending on the class of user an individual is in, the individual may want different text box settings that are more useful to the individual based on the individual's current state or cohort (autism, child, pre-Alzheimer's, etc.) and/or emotional style, etc. For example, Maja is better suited to standard text box settings, while Cliff or someone with autism is better suited to text box settings with a different GUI, spacing, arrangement, sizing, etc. The system can learn what text box settings are best for different cohorts (classes of user) so that other users can benefit as the system learns.

Figure 3:
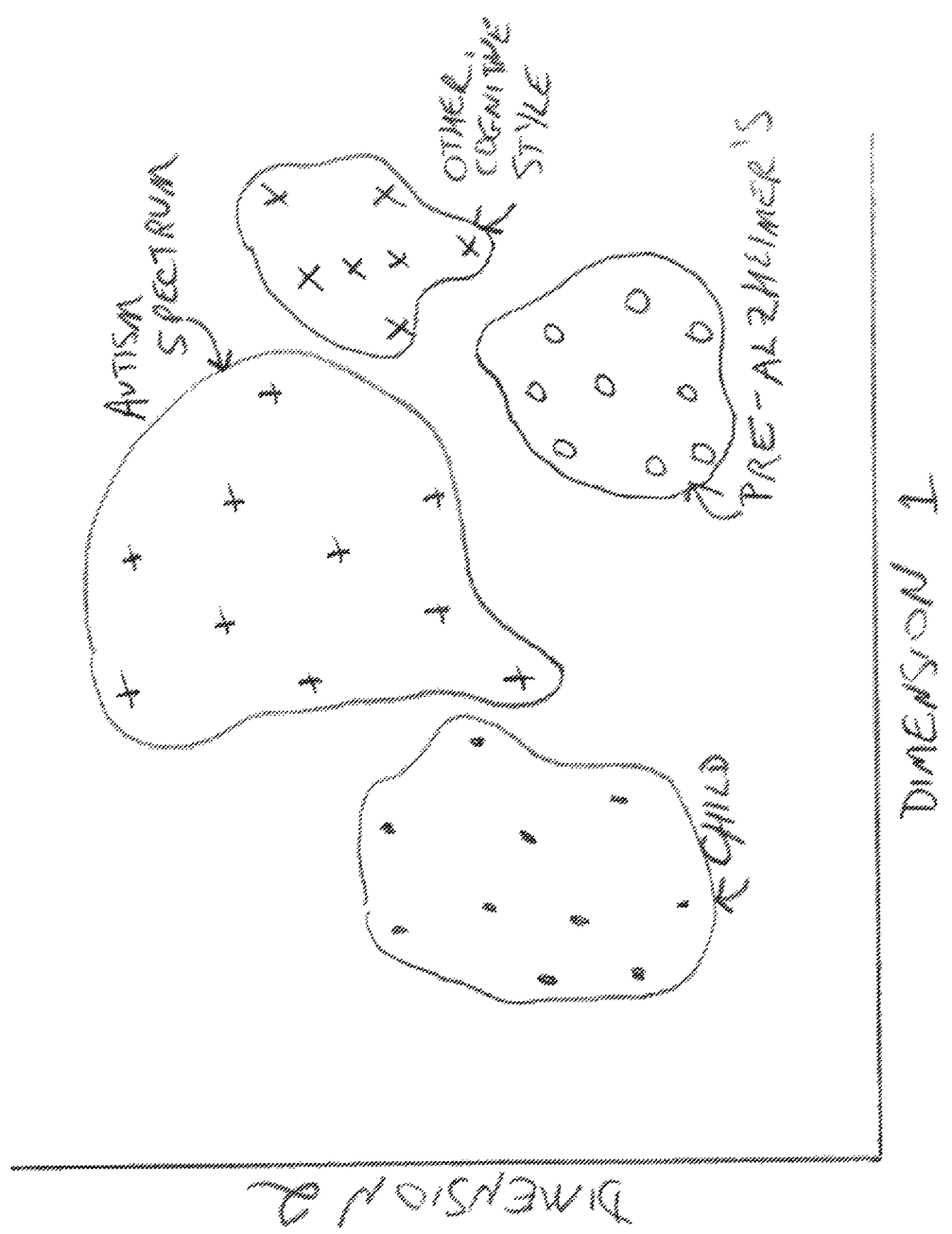
FIG. 3 is a graph illustrating three cohorts, clustered according to the effectiveness or "desirability" of the text box settings for two dimensions of characteristics.

A user can tap on a certain style of text box settings when the user "likes" it. In another embodiment, the system determines (with a certain level of confidence) that a user is becoming impatient, nervous, etc. FIG. 3 is a graph illustrating three cohorts, clustered according to the effectiveness or "desirability" of the text box settings for two dimensions of characteristics. Various approaches are possible for estimating a user's emotional state. For example, a camera on the electronic device is used with face-tracking technology to allow the system to read facial expressions and identify the user' emotional state.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 4:
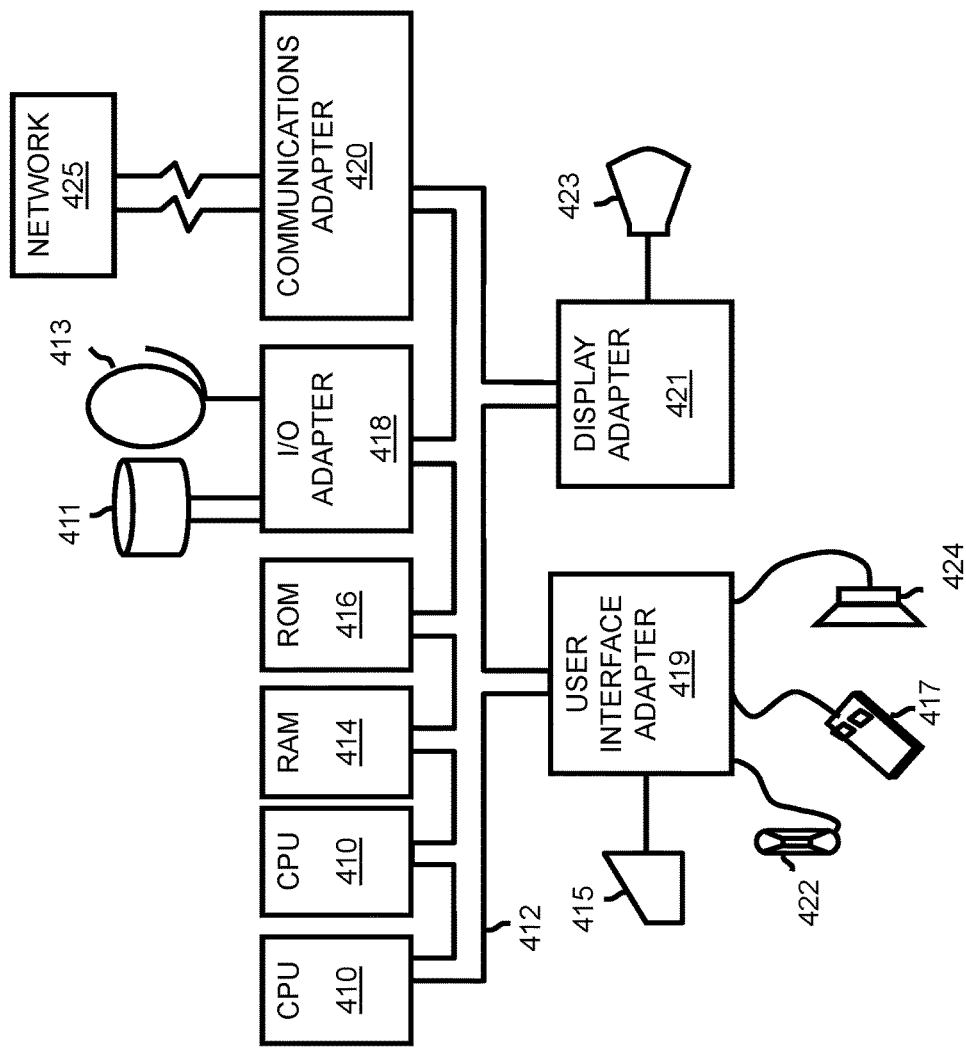
FIG. 4 is a diagram illustrating a computer program product for displaying a text box on a display screen of an electronic device according to an embodiment of the invention.

Referring now to FIG. 4, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 410. The CPUs 410 are interconnected with system bus 412 to various devices such as a random access memory (RAM) 414, read-only memory (ROM) 416, and an input/output (I/O) adapter 418. The I/O adapter 418 can connect to peripheral devices, such as disk units 411 and tape drives 413, or other program storage devices that are readable by the system. The system can read the inventive instructions on the program storage devices and follow these instructions to execute the methodology of at least one embodiment of the invention. The system further includes a user interface adapter 419 that connects a keyboard 415, mouse 417, speaker 424, microphone 422, and/or other user interface devices such as a touch screen device (not shown) to the bus 412 to gather user input. Additionally, a communication adapter 420 connects the bus 412 to a data processing network 425, and a display adapter 421 connects the bus 412 to a display device 423 which may be embodied as an output device such as a monitor, printer, or transmitter, for example.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
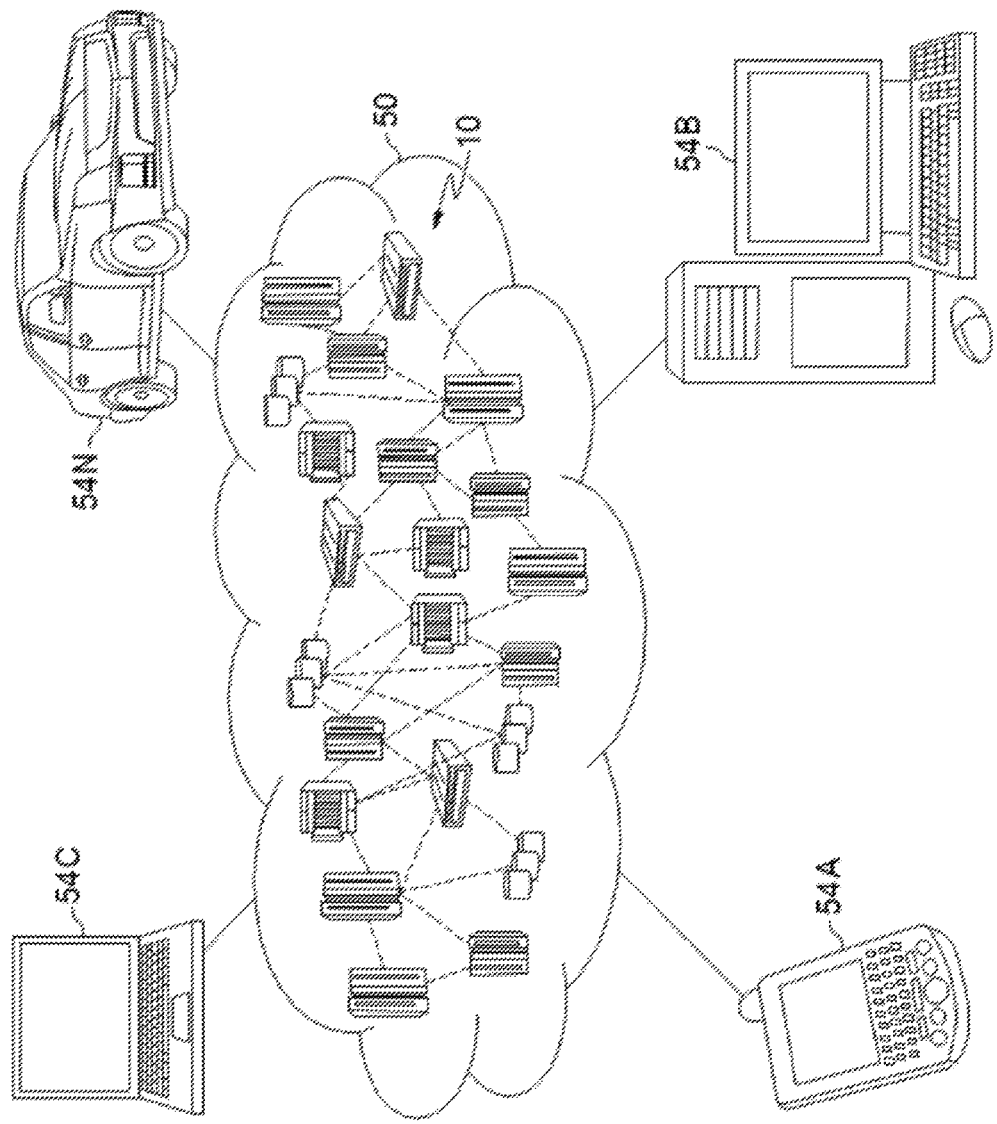
FIG. 5 depicts a cloud computing environment according to an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
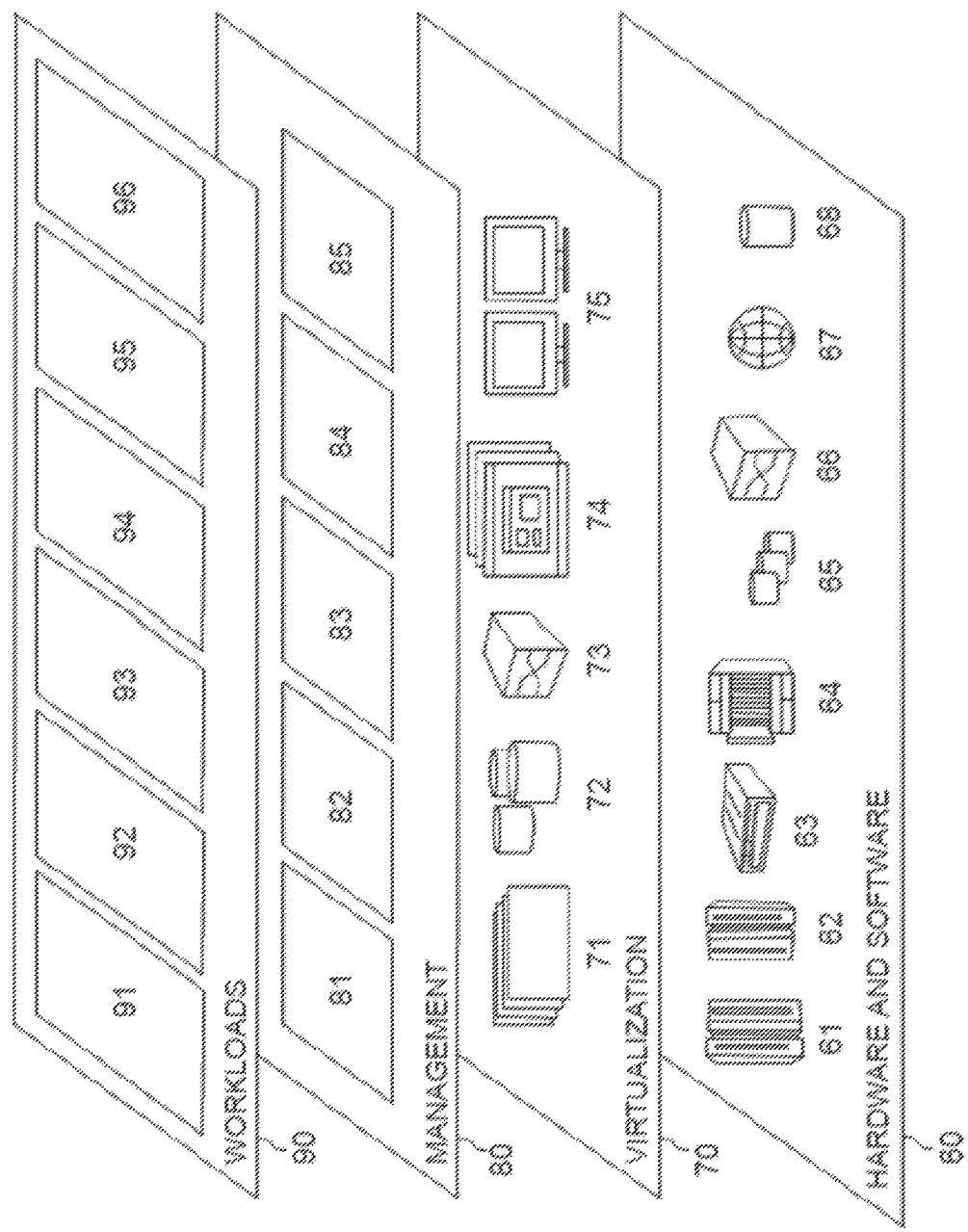
FIG. 6 depicts abstraction model layers according to an embodiment of the present invention.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and cursor and cursor-hover based on user state or sentiment analysis 96.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for displaying a text box on a display screen of an electronic device, said method comprising:
    determining a state of a user with an input device including at least one of a camera, a keyboard, and a mouse;
    modifying a text box setting on the electronic device with a processor connected to the input device based on the state of the user, said modifying of the text box setting including modifying an amount of visual information in the text box, modifying an amount of audible information played with the text box, and modifying an amount of time required to display the text box; and
    displaying the text box on the display screen of the electronic device when a pointer is within a threshold degree of proximity to an item on the display screen for the amount of time required to display the text box, wherein the state of the user is determined from a facial expression of the user, a degree of multitasking of the user, information from a calendar of the user, brain waves of the user, and skin conductivity of the user.

2. The method according to claim 1, wherein the state of the user includes at least one of fatigue, frustration, distracted, autistic, youth, Alzheimer's, pre-Alzheimer's, learning disability, and attention deficit hyperactivity disorder.

3. The method according to claim 1, wherein the state of the user is selected from a group consisting of fatigue, frustration, distracted, autistic, youth, Alzheimer's, pre-Alzheimer's, learning disability, and attention deficit hyperactivity disorder.

4. The method according to claim 1, wherein said modifying of the text box setting on the electronic device includes decreasing the amount of visual information in the text box, increasing the amount of audible information in the text box, and decreasing the amount of time required to display the text box when the state of the user includes at least one of fatigue, frustration, distracted, autistic, youth, Alzheimer's, pre-Alzheimer's, learning disability, and attention deficit hyperactivity disorder.

5. The method according to claim 1, further comprising determining the degree of multitasking of the user from a rate of switching between applications on the electronic device, a rate of switching between windows on the electronic device, a number of open applications on the electronic device, a number of open windows on the electronic device, and information from the calendar of the user.

6. The method according to claim 1, further comprising creating a composite text box when the user drags a first text box to a position proximate a second text box, the composite text box including: information from the first text box; information from the second text box; and information describing how the first text box relates to the second text box.

7. The method according to claim 6, further comprising automatically displaying the composite text box on the display screen when one of display of the first text box is triggered and display of the second text box is triggered.

8. The method according to claim 1, further comprising:
identifying that a pop-up text box satisfies a threshold degree of importance based on the state of the user; and
displaying the pop-up text box on the display screen of the electronic device when the pointer is not within the threshold degree of proximity to the item on the display screen for the amount of time required to display the text box.

9. The method according to claim 1, further comprising modifying the text box setting on the electronic device based on a profile of the user, the profile of the user including a browsing history of the user, purchasing history of the user, application history of the user, text box history of the user, electronic bookmarks of the user, likes, and interests of the user.

10. The method according to claim 1, wherein said modifying of the text box setting on the electronic device includes selecting content to be displayed in the text box based on the emotional state of the user.

11. The method according to claim 1, wherein the input device includes a brain wave monitor.

12. A electronic device for displaying a text box on a display screen, said electronic device comprising:
processing circuitry configured to
determine a state of a user with an input device including at least one of a camera, a keyboard, and a mouse,
modify a text box setting based on the state of the user, said modifying of the text box setting including modifying an amount of visual information in the text box, modifying an amount of audible information played with the text box, and modifying an amount of time required to display the text box, and
display the text box on the display screen when a pointer is within a threshold degree of proximity to an item on the display screen for the amount of time required to display the text box, wherein the state of the user is determined from a facial expression of the user, a degree of multitasking of the user, information from a calendar of the user, and brain waves of the user.

13. The electronic device according to claim 12, wherein the state of the user includes at least one of fatigue, frustration, distracted, autistic, youth, Alzheimer's, pre-Alzheimer's, learning disability, and attention deficit hyperactivity disorder.

14. The electronic device according to claim 12, wherein said modifying of the text box setting includes at least one of:

decreasing the amount of visual information in the text box when the state of the user includes at least one of fatigue, frustration, distracted, autistic, youth, Alzheimer's, pre-Alzheimer's, learning disability, and attention deficit hyperactivity disorder;
increasing the amount of audible information in the text box when the state of the user includes at least one of fatigue, frustration, distracted, autistic, youth, Alzheimer's, pre-Alzheimer's, learning disability, and attention deficit hyperactivity disorder; and
decreasing the amount of time required to display the text box when the state of the user includes at least one of fatigue, frustration, distracted, autistic, youth, Alzheimer's, pre-Alzheimer's, learning disability, and attention deficit hyperactivity disorder.

15. The electronic device according to claim 12, wherein the processing circuitry is further configured to determine the degree of multitasking of the user from at least one of a rate of switching between applications on the electronic device, a rate of switching between windows on the electronic device, a number of open applications on the electronic device, a number of open windows on the electronic device, and information from the calendar of the user.

16. The electronic device according to claim 12, wherein the processing circuitry is further configured to create a composite text box when the user drags a first text box to a position proximate a second text box, the composite text box including at least one of: information from the first text box and information from the second text box; and information describing how the first text box relates to the second text box.

17. The electronic device according to claim 16, wherein the processing circuitry is further configured to display the composite text box on the display screen when one of display of the first text box is triggered and display of the second text box is triggered.

18. The electronic device according to claim 12, wherein the processing circuitry is further configured to modify the text box setting based on a profile of the user, the profile of the user including from at least one of a browsing history of the user, purchasing history of the user, application history of the user, text box history of the user, electronic bookmarks of the user, likes, and interests of the user.

19. The electronic device according to claim 12, wherein the processing circuitry is further configured to learn text box settings that are best for different groups of users.

20. A non-transitory computer-readable medium having computer-readable instructions stored thereon which when executed by a computer cause the computer to perform a method for displaying a text box on a display screen of an electronic device, said method comprising:
determining a state of a user;
modifying a text box setting on the electronic device based on the state of the user, said modifying including modifying modifies an amount of visual information in the text box, modifying an amount of audible information played with the text box, and modifying an amount of time required to display the text box; and
displaying the text box when a pointer is within a threshold degree of proximity to an item on a display screen for the amount of time required to display the text box, wherein the state of the user is determined from a facial expression of the user, a degree of multitasking of the user, information from a calendar of the user, and brain waves of the user.

* * * * *